US012159709B2

(12) United States Patent
Baker

(10) Patent No.: US 12,159,709 B2
(45) Date of Patent: Dec. 3, 2024

(54) COMPUTER-IMPLEMENTED METHOD OF ORGANIZING HOSPITAL STAFFING AND MEDICAL INFORMATION ACROSS MULTIPLE DEPARTMENTS

(71) Applicant: Carley Baker, Saline, MI (US)

(72) Inventor: Carley Baker, Saline, MI (US)

( * ) Notice: Subject to any disclaimer, the term of this patent is extended or adjusted under 35 U.S.C. 154(b) by 0 days.

(21) Appl. No.: 18/131,168

(22) Filed: Apr. 5, 2023

(65) Prior Publication Data
US 2023/0335263 A1    Oct. 19, 2023

Related U.S. Application Data

(60) Provisional application No. 63/331,342, filed on Apr. 15, 2022.

(51) Int. Cl.
*G06F 3/0482* (2013.01)
*G06F 3/0484* (2022.01)
*G16H 40/20* (2018.01)

(52) U.S. Cl.
CPC .......... *G16H 40/20* (2018.01); *G06F 3/0482* (2013.01); *G06F 3/0484* (2013.01)

(58) Field of Classification Search
CPC ................................................ G06F 3/048–05
See application file for complete search history.

(56) References Cited

U.S. PATENT DOCUMENTS

| | | | |
|---|---|---|---|
| 6,336,053 B1* | 1/2002 | Beatty | G05B 19/4188 715/967 |
| 9,591,481 B1* | 3/2017 | Fisher | H04B 7/0413 |
| 9,597,160 B1* | 3/2017 | Gregg, II | A61B 34/25 |
| 10,191,626 B2 | 1/2019 | Dorn | |
| 10,262,382 B2 | 4/2019 | Moore | |
| 10,698,922 B2* | 6/2020 | Bormann | G16H 10/60 |
| 10,762,983 B2 | 9/2020 | Fewins | |
| 10,922,775 B2 | 2/2021 | Moore | |
| 11,004,547 B2 | 5/2021 | Valdes | |
| 2005/0055243 A1* | 3/2005 | Arndt | G16H 10/60 705/2 |
| 2007/0016442 A1* | 1/2007 | Stroup | G06Q 10/10 705/2 |
| 2007/0100870 A1* | 5/2007 | Jenkins | G06F 16/9535 707/999.102 |
| 2007/0143136 A1* | 6/2007 | Moore, III | G16H 50/20 705/2 |
| 2007/0276701 A1* | 11/2007 | Suzuki | G16H 70/20 705/3 |
| 2008/0270240 A1* | 10/2008 | Chu | G06Q 30/0239 434/350 |
| 2009/0076845 A1* | 3/2009 | Bellin | G16H 40/20 715/781 |
| 2010/0036676 A1* | 2/2010 | Safdi | G16H 15/00 705/2 |

(Continued)

*Primary Examiner* — Daniel Rodriguez
(74) *Attorney, Agent, or Firm* — Emily Darrigrand; NCCU IP Clinic

(57) ABSTRACT

A computer-implemented method provides hospital staff with a single point of access to names and contact information for staff members across multiple departments, and providing the staff the ability to quickly determine what a patient is scheduled to receive from a department at any given time, and accurately identify which staff members of each department are assigned to a patient.

21 Claims, 23 Drawing Sheets

(56) References Cited

U.S. PATENT DOCUMENTS

| | | | |
|---|---|---|---|
| 2010/0235815 A1* | 9/2010 | Maybee | G06F 11/3636 717/125 |
| 2010/0332255 A1* | 12/2010 | Rotunda | G16H 40/20 715/753 |
| 2011/0046974 A1* | 2/2011 | Burks | G16H 10/40 715/764 |
| 2012/0066000 A1* | 3/2012 | Opfer | G16H 10/60 705/3 |
| 2012/0130730 A1* | 5/2012 | Setlur | G16H 40/20 705/2 |
| 2012/0259659 A1* | 10/2012 | Fotheringham | G06Q 10/10 705/3 |
| 2013/0018666 A1* | 1/2013 | Murphy | A61B 17/58 705/2 |
| 2013/0123973 A1* | 5/2013 | Saranow | G06Q 30/0621 700/233 |
| 2013/0132108 A1* | 5/2013 | Solilov | G16H 50/70 705/2 |
| 2015/0113422 A1* | 4/2015 | Pfeiffer | H04L 67/10 715/739 |
| 2015/0213211 A1* | 7/2015 | Zaleski | G06F 3/0482 715/753 |
| 2015/0310362 A1* | 10/2015 | Huffman | G06Q 10/0633 705/2 |
| 2016/0323417 A1* | 11/2016 | Spear | H04L 67/10 |
| 2017/0032092 A1* | 2/2017 | Mink | G06Q 10/1095 |
| 2017/0076046 A1* | 3/2017 | Barnes | G16H 10/60 |
| 2018/0046768 A1* | 2/2018 | Paskett | G16H 10/60 |
| 2020/0001112 A1* | 1/2020 | Chiu | A61N 5/103 |
| 2021/0216259 A1* | 7/2021 | Ullmann | G06F 3/1238 |
| 2021/0335486 A1* | 10/2021 | Cunningham | G06Q 30/0206 |
| 2021/0398680 A1* | 12/2021 | Velamuri | G16H 50/30 |
| 2022/0020476 A1* | 1/2022 | Souissi | G16H 40/20 |

\* cited by examiner

Continuous Coordination

Name last, first, middle
DOB yyyy-mm-dd (age #)
Sex M/F
Height # ft # in
Weight # lb MRN #
Admit Date yyyy-mm-dd
Code Status F/P/DNR
Class Inpat/Output
Allergies Yes/No FIN #
Assigned Room #
Attending Physician last, first (x#)
Bedside Nurse last, first (x#)
Current Location #

ACTIVE PATIENTS

Barry, James Michael
Branch, Ann Lorie
Cline, Imelda Kristin
Conrad, Allen Jeff
Dillon, Catherine Anne
Faulkner, Andrews Tyler
Foley, Alfredo Brendan
Gardner, Deborah Emily
Gordon, Michael Carlton
Hardin, Elisabeth Kate
Hester, Herschel Samuel
Horne, Walton Trevor
Johns, Luis Ricardo

| SURGERY |
| RADIOLOGY |
| LABORATORY |
| PHARMACY |
| DIALYSIS |
| TELEMETRY |
| THERAPY |

All Departments

All Patients

Logged in as DEMO

Friday, Dec 23 2022 09:10:02 AM

FIG. 3

Continuous Coordination

Name: Barry, James Michael
DOB 1850-02-17 (age 72)
Sex M
Height 5 ft 7.75 in
Weight 201.5 lb MRN 8325088
Admit Date 2022-12-18
Code Status DNR
Class Outpatient
Allergies No FIN 379205
Assigned Room 3034
Attending Physician Donaldson, Noel (x8859)
Bedside Nurse Sullivan, Tommy (x4211)
Current Location 3034

602 — ACTIVE PATIENTS
- Barry, James Michael
- Branch, Ann Lorie
- Cline, Imelda Kristin
- Conrad, Allen Jeff
- Dillon, Catherine Anne
- Faulkner, Andrews Tyler
- Foley, Alfredo Brendan
- Gardner, Deborah Emily
- Gordon, Michael Carlton
- Hardin, Elisabeth Kate
- Hester, Harschel Samuel
- Horne, Walton Trevor
- Johns, Luis Ricardo

| SURGERY |
| RADIOLOGY |
| LABORATORY |
| PHARMACY |
| DIALYSIS |
| TELEMETRY |
| THERAPY |

All Patients — 604
All Departments — 608
610

Logged in as DEMO
Friday, Dec 23 2022 06:12:36 AM

FIG. 6

Continuous Coordination

Name Barry, James Michael
DOB 1950-02-17 (age 72)
Sex M
Height 5 ft 7.75 in
Weight 201.5 lb MRN 8325088
Admit Date 2022-12-18
Code Status DNR
Class Outpatient
Allergies No FIN 379205
Assigned Room 3034
Attending Physician Donaldson, Noel (x8858)
Bedside Nurse Sullivan, Tommy (x4211)
Current Location 3034

ACTIVE PATIENTS — 802

Barry, James Michael
Branch, Ann Lorie
Cline, Imelda Kristin
Conrad, Allen Jeff
Gardner, Deborah Emily
Hardin, Elisabeth Kate
Morales, Rosa Luisa
Pittman, Louise Tina
Reid, Jordan Whitney
Robinson, Wayne Larry
Salinas, Albert Patrick

812 —
SURGERY
RADIOLOGY
LABORATORY
PHARMACY
DIALYSIS
TELEMETRY
THERAPY

SURGERY INFORMATION

Patient Name   Barry, James Michael
Procedure      Tonsillectomy
Scheduled Time 13:00
ETC            150
Estimated Wait 2 hr 30 min
Room           105
Surgeon        Potter, Roxanne (x9072)
Anesthesiologist Henry, Kristy (x2180)
Pre-Op         Edwards, Frances (x3607)

All Patients — 804
All Departments — 808
810
814
806
System of Record

Logged in as DEMO          Friday, Dec 23 2022 06:12:39 AM

FIG. 8A

Continuous Coordination

Name Barry, James Michael
DOB 1950-02-17 (age 72)
Sex M
Height 5 ft 7.75 in
Weight 201.5 lb MRN 8325088
Admit Date 2022-12-18
Code Status DNR
Class Outpatient
Allergies No FIN 379205
Assigned Room 3034
Attending Physician Donaldson, Noel (x8858)
Bedside Nurse Sullivan, Tommy (x4211)
Current Location 3034

ACTIVE PATIENTS
Branch, Ann Lorie
Cline, Imelda Kristin
Dillon, Catherine Anne
Faulkner, Andrews Tyler
Foley, Alfredo Brendan
Gardner, Deborah Emily
Gordon, Michael Carlton
Hardin, Elisabeth Kate
Johns, Luis Ricardo
Mercer, Edward Sonny
Morales, Rosa Luisa
Riley, Daniela Jenny 812 — SURGERY / RADIOLOGY / LABORATORY / PHARMACY / DIALYSIS / TELEMETRY / THERAPY

RADIOLOGY INFORMATION

NO INFORMATION — 814

All Patients | All Departments

Logged in as DEMO | Friday, Dec 23 2022 06:09:49 AM

FIG. 8B

Continuous Coordination

Name last, first, middle
DOB yyyy-mm-dd (age #)
Sex M/F
Height # ft # in
Weight # lb

MRN #
Admit Date yyyy-mm-dd
Code Status F/P/DNR
Class Inpat/Outpat
Allergies Yes/No

FIN #
Assigned Room #
Attending Physician last, first (x#)
Bedside Nurse last, first (x#)
Current Location #

ACTIVE PATIENTS — 1104
- Barry, James Michael
- Branch, Ann Lorie
- Cline, Imelda Kristin
- Conrad, Allen Jeff
- Gardner, Deborah Emily
- Hardin, Elisabeth Kate
- Morales, Rosa Luisa
- Pittman, Louise Tina
- Reid, Jordan Whitney
- Robinson, Wayne Larry
- Salinas, Albert Patrick

Departments (1106, 1108): SURGERY (1110), RADIOLOGY, LABORATORY, PHARMACY, DIALYSIS, TELEMETRY, THERAPY

SURGERY INFORMATION — 1112

| | |
|---|---|
| Patient Name | Gardner, Deborah Emily |
| Procedure | Biopsy |
| Scheduled Time | 06:00 |
| ETC | 120 |
| Estimated Wait | 2 hr 0 min |
| Room | 104 |
| Surgeon | Snyder, Stacy (x9126) |
| Anesthesiologist | Chen, Garry (x6192) |
| Pre-Op | Dyer, Vincent (x8269) |

| | |
|---|---|
| Patient Name | Hardin, Elisabeth Kate |
| Procedure | Carotid Endarterectomy |
| Scheduled Time | 07:30 |

All Patients — 1102
All Departments
System of Record

Logged in as DEMO  Friday, Dec 23 2022 06:10:42 AM

FIG. 11

Continuous Coordination

ACTIVE PATIENTS — 1302
- Barry, James Michael
- Branch, Ann Lorie
- Cline, Imelda Kristin
- Conrad, Allen Jeff
- Gardner, Deborah Emily
- Hardin, Elisabeth Kate
- Morales, Rosa Luisa
- Pittman, Louise Tina
- Reid, Jordan Whitney
- Robinson, Wayne Larry
- Salinas, Albert Patrick Name: Conrad, Allen Jeff
DOB: 1984-11-12 (age 38)
Sex: M
Height: 6 ft 2.25 in
Weight: 203.5 lb MRN: 6879059
Admit Date: 2022-12-18
Code Status: Full
Class: Inpatient
Allergies: No FIN: 379205
Assigned Room: 2036
Attending Physician: Aguilar, Madelyn (x8210)
Bedside Nurse: Campbell, Darin (x4776)
Current Location: 2036

1306

| SURGERY |
| RADIOLOGY |
| LABORATORY |
| PHARMACY |
| DIALYSIS |
| TELEMETRY |
| THERAPY |

SURGERY INFORMATION — 1312
Patient Name: Conrad, Allen Jeff
Procedure: Gastroenterostomy
Scheduled Time: 14:00
ETC: 105
Estimated Wait: 1 hr 45 min
Room: 108
Surgeon: Roman, Alyssa (x3671)
Anesthesiologist: Lin, Jimmy (x3965)
Pre-Op: Harding, Rolland (x5413)

All Patients — 1304
All Departments — 1308
System of Record — 1310

Logged in as DEMO            Friday, Dec 23 2022 06:21:55 AM

FIG. 13

Continuous Coordination

Name Dillon, Catherine Anne  MRN 2842613  FIN 379205
DOB 1953-06-28 (age 69)  Admit Date 2022-12-17  Assigned Room 2023
Sex F  Code Status Full  Attending Physician Castillo, Colleen (x9857)
Height 5 ft 11 in  Class Inpatient  Bedside Nurse Winters, Odessa (x6332)
Weight 147.75 lb  Allergies Yes  Current Location 2023

ACTIVE PATIENTS — 1402

Branch, Ann Lorie
Cline, Imelda Kristin
Dillon, Catherine Anne
Faulkner, Andrews Tyler
Foley, Alfredo Brendan
Gardner, Deborah Emily
Gordon, Michael Carlton
Hardin, Elisabeth Kate
Johns, Luis Ricardo
Mercer, Edward Sonny
Morales, Rosa Luisa
Riley, Daniela Jenny

| SURGERY |
| RADIOLOGY |
| LABORATORY |
| PHARMACY |
| DIALYSIS |
| TELEMETRY |
| THERAPY |

RADIOLOGY INFORMATION — 1404

Patient Name  Dillon, Catherine Anne
Ordered Imaging  CAT (Right Arm)
Scheduled Time  07:00
Estimated Wait  0 hr 37 min
Queue  0
Room  228
At Bedside  No
Radiologist  McMillan, Cassandra (x7933)
Transport Tech  Moore, Ilene (x8844)

All Patients  All Departments  System of Record

Logged in as DEMO  Friday, Dec 23 2022 06:22:32 AM

FIG. 14

Continuous Coordination

Name Foley, Alfredo Brendan
DOB 1964-07-29 (age 58)
Sex M
Height 5 ft 2 in
Weight 167.0 lb

MRN 2573851
Admit Date 2022-12-20
Code Status DNR
Class Outpatient
Allergies No

FIN 379205
Assigned Room 2116
Attending Physician Jordan, Nell (x2571)
Bedside Nurse Lane, Nettie (x9595)
Current Location 2116

ACTIVE PATIENTS
Branch, Ann Lorie
Cline, Imelda Kristin
Conrad, Allen Jeff
Faulkner, Andrews Tyler
Foley, Alfredo Brendan — 1502
Hester, Herschel Samuel
Horne, Walton Trevor
Mercer, Edward Sonny
Morales, Rosa Luisa
Reid, Jordan Whitney
Riley, Daniela Jenny
Salinas, Albert Patrick

| SURGERY |
| RADIOLOGY |
| LABORATORY |
| PHARMACY |
| DIALYSIS |
| TELEMETRY |
| THERAPY |

LABORATORY INFORMATION — 1504
Patient Name Foley, Alfredo Brendan
Lab Order Hematocrit Test
Scheduled Time 11:00
Estimated Wait 4 hr 37 min
Queue 0
STAT 0
Phlebotomist Haney, Otis (x6633)

All Patients | All Departments | System of Record

Logged in as DEMO | Friday, Dec 23 2022 06:23:04 AM

FIG. 15

Continuous Coordination

Name Hester, Herschel Samuel
DOB 1970-05-18 (age 52)
Sex M
Height 5 ft 2.5 in
Weight 178.0 lb

MRN 7381818
Admit Date 2022-12-20
Code Status Partial
Class Inpatient
Allergies Yes

FIN 379205
Assigned Room 2109
Attending Physician Baxter, Felicia (x9873)
Bedside Nurse Lam, Jimmie (x7299)
Current Location 2109

ACTIVE PATIENTS
- Conrad, Allen Jeff
- Dillon, Catherine Anne
- Faulkner, Andrews Tyler
- Foley, Alfredo Brendan
- Hester, Herschel Samuel — 1602
- Johns, Luis Ricardo
- Morales, Rosa Luisa
- Mercer, Edward Sonny
- Riley, Daniela Jenny
- Pittman, Louise Tina
- Robinson, Wayne Larry
- Salinas, Albert Patrick All Patients

| SURGERY |
| RADIOLOGY |
| LABORATORY |
| PHARMACY |
| DIALYSIS |
| TELEMETRY |
| THERAPY |

All Departments

PHARMACY INFORMATION — 1604

Patient Name Hester, Herschel Samuel
Medication Details Crestor (Rosuvastatin)
Scheduled Time 08:58
Estimated Wait 2 hr 34 min
Queue 0
Status OUT FOR HAND DELIVERY
Est Arrival Time 10:58
Pharmacist Franco, Rachael (x4271)

System of Record

Logged in as DEMO    Friday, Dec 23 2022 06:23:59 AM

Continuous Coordination

Name Horne, Walton Trevor
DOB 1975-02-27 (age 47)
Sex M
Height 6 ft 3 in
Weight 194.5 lb MRN 3829086
Admit Date 2022-12-18
Code Status Partial
Class Outpatient
Allergies No FIN 379205
Assigned Room 3015
Attending Physician Dunn, Aimee (x4288)
Bedside Nurse Glass, Kaye (x8722)
Current Location 3015

ACTIVE PATIENTS — 1702
- Branch, Ann Lorie
- Conrad, Allen Jeff
- Horne, Walton Trevor
- Morales, Rosa Luisa
- Reid, Jordan Whitney
- Salinas, Albert Patrick

| SURGERY |
| RADIOLOGY |
| LABORATORY |
| PHARMACY |
| DIALYSIS |
| TELEMETRY |
| THERAPY |

DIALYSIS INFORMATION — 1704

Patient Name  Horne, Walton Trevor
Dialysis Order  Peritoneal Dialysis
Scheduled Time  08:30
Estimated Wait  2 hr 5 min
Queue  0
Nurse  Maynard, Tonya (x1221)
Transport Tech  Holder, Peggy (x7795)

All Patients    All Departments    System of Record

Logged in as DEMO                  Friday, Dec 23 2022 06:24:41 AM

Continuous Coordination

Name Foley, Alfredo Brendan
DOB 1964-07-29 (age 58)
Sex M
Height 5 ft 2 in
Weight 167.0 lb MRN 2573851
Admit Date 2022-12-20
Code Status DNR
Class Outpatient
Allergies No FIN 379205
Assigned Room 2116
Attending Physician Jordan, Nell (x2571)
Bedside Nurse Lane, Nettie (x0595)
Current Location 2116

ACTIVE PATIENTS
Barry, James Michael
Branch, Ann Lorie
Conrad, Allen Jeff
Foley, Alfredo Brendan — 1902
Gordon, Michael Carlton
Mercer, Edward Sonny
Pittman, Louise Tina
Salinas, Albert Patrick

SURGERY
RADIOLOGY
LABORATORY
PHARMACY
DIALYSIS
TELEMETRY
THERAPY

THERAPY INFORMATION — 1904

Ordered Therapy  Speech
Scheduled Time   14:00
Estimated Wait   6 hr 45 min
Queue            1
Tech             Hogan, Amber (x1299)

Patient Name     Foley, Alfredo Brendan
Order Therapy    Physical
Scheduled Time   16:00
Estimated Wait   8 hr 45 min
Queue            2
Tech             George, Jessica (x9456)

System of Record

All Patients    All Departments

Logged in as DEMO    Friday, Dec 23 2022 07:15:30 AM

FIG. 19B

COMPUTER-IMPLEMENTED METHOD OF ORGANIZING HOSPITAL STAFFING AND MEDICAL INFORMATION ACROSS MULTIPLE DEPARTMENTS

CROSS-REFERENCE TO RELATED APPLICATIONS

This application claims the benefit of U.S. Provisional Application No. 63/331,342, filed on Apr. 15, 2022, which is hereby incorporated in its entirety.

FIELD OF THE INVENTION

The present invention is directed to a computer-implemented method that provides hospital staff with a single point of access to names and contact information for staff members across multiple departments. More particularly, the present invention is directed to displaying scheduled procedures for patients, assigned staff for each procedure, and corresponding departments for the procedures.

BACKGROUND

The following description is not an admission that any of the information provided herein is prior art or relevant to the present invention, or that any publication specifically or implicitly referenced is prior art. Any publications cited in this description are incorporated by reference herein. Where a definition or use of a term in an incorporated reference is inconsistent or contrary to the definition of that term provided herein, the definition of that term provided herein applies and the definition of that term in the reference does not apply.

Currently, a challenge that many healthcare professionals face is disorganization of staffing contact information. Within any given hospital, there is very little communication between respective departments. The lack of internal communications can: 1) create delays in patients being attended to by their appropriate providers in a timely fashion; 2) delay or cancel medical treatments due to poor staff coordination and teamwork; and 3) lead to negative health outcomes and poor patient satisfaction.

Healthcare tools that are currently in use list individual staff names and contact numbers, but these tools are used within a single department. Consequently, hospital staff often need to call the clerk of a department or floor and wait to be transferred to the employee to whom they wish to speak. This process causes delays when the intended employee cannot be contacted directly. Furthermore, staff often have little insight into the anticipated time for a patient's procedure or treatment, so they routinely have to call and interrupt staff from the procedure floor to determine the scheduled time slot.

Therefore, there exists a need for a computer-implemented method that does not have the aforementioned limitations and provides caregivers a computer-implemented method that is easy to use, while substantially capturing information from multiple sources and displaying all of the information in a single location.

SUMMARY OF THE INVENTION

The present invention is directed to a computer-implemented method that provides hospital staff with a single point of access to names and contact information for staff members across multiple departments. Furthermore, the staff will be able to quickly determine what a patient is scheduled to receive from a department, when a patient is scheduled to receive care from a department, where a patient is in the queue lineup, and accurately identify which staff members of each department are assigned to a patient.

In one embodiment, a computer-implemented method for providing a user of a computing device access to patient information and scheduled procedures, the method comprises the following steps: receiving by one or more peripherals, a user input, the user input indicating a user command to affect a login screen and a main screen; the main screen displaying data information received from a connected patient database, the displayed information comprising a list of patient names and a list of departments; receiving by one or more peripherals, a user selection of a patient name from the list of patient names; filtering data information from the patient database displaying the selected patient's information in response to the user's selection of the patient name; receiving by one or more peripherals, user selection of an all-patients button, removing the filter for the selected patient from the data; receiving by one or more peripherals, a user selection of a department from the list of departments; filtering the data information from the patient database displaying the selected patient's procedure's available for the selected department on the main screen in response to the user selection of the department; and receiving by one or more peripherals, user selection of an all-departments button, removing the filter for the selected department from the data.

In a further embodiment, the login screen comprises a username field and a password field, and the username field and password field are configured to receive user input.

In still a further embodiment, the login screen comprises a confirmation button for checking the login information entered into the username field and the password field.

In still a further embodiment, the login screen is configured to display a message for issues with the user input in the username and/or password fields.

In a further embodiment, the method further comprises options for the user to logout out of the computer-implemented method. In one embodiment, a yes option logs user out and a no option keeps the user logged in.

In a further embodiment, the main task screen is configured to display an updating date display.

In a further embodiment, the main task screen is configured to display an area showing a username for the user.

In another embodiment, a computer-implemented method for providing a user of a computing device access to patient information and scheduled procedures, the method comprising: receiving by one or more peripherals, user input, the user input indicating a user command to affect a login screen and a main screen; displaying information received from a connected patient database, wherein the displayed information comprises a list of patient names and a list of departments; receiving by one or more peripherals, a user selection of a department from the list of departments; filtering the information from the patient database displaying a list of filtered patients based on the selected department in response to the user selection of the department; receiving by one or more peripherals, a user selection of an all-departments button, removing the filter for the selected department from the data; receiving by one or more peripherals, a user selection of a patient name from the list of filtered patient names; filtering information from the patient database displaying the selected patient's information and the selected patient's procedure information for the selected department in response to the user's selection of the patient name; and receiving by one or more peripherals, a user selection of an all-patients button, removing the filter for the selected patient from the data.

In a further embodiment, the login screen comprises a username field and a password field, and the username field and password field are configured to receive user input.

In still a further embodiment, the login screen comprises a confirmation button for checking the login information entered into the username field and the password field.

In still a further embodiment, the login screen is configured to display a message for issues with the user input in the username and/or password fields.

In a further embodiment, the method further comprises options for the user to logout out of the computer-implemented method. In one embodiment, a yes option logs user out and a no option keeps the user logged in.

In a further embodiment, the main task screen is configured to display an updating date display.

In a further embodiment, the main task screen is configured to display an area showing a username for the user.

Various objects, features, aspects, and advantages of the inventive subject matter will become more apparent from the following detailed description of exemplary configuration, along with the accompanying figures in which like numerals represent like components.

BRIEF DESCRIPTION OF THE DRAWINGS

The present invention is described in detail below with reference to the attached drawings figures, wherein:

FIGS. 2A-2D are exemplary configurations of the method in FIG. 1, which depicts a login screen for the computer-implemented method.

FIG. 3 is an exemplary configuration of the present invention, which depicts an unfiltered screen of all patients in a database.

FIG. 6 is an exemplary configuration of the method in FIG. 5, which depicts a filtered screen of patients in the database.

FIGS. 8A-B are exemplary configurations of the method in FIG. 7, which depict a filtered screen of patients and a patient's procedure information.

FIG. 11 is an exemplary configuration of the method in FIG. 10, which depicts a filtered screen based on a selected department and procedure information for all filtered patients.

FIGS. 13-19B are exemplary configurations of the method in FIG. 12, which depict a patient's procedure information based on a selected department.

DETAILED DESCRIPTION

As used in the description herein, the meaning of "a," "an," and "the" includes plural reference unless the context clearly dictates otherwise. Also, as used in the description herein, the meaning of "in" includes "into" and "on" unless the context clearly dictates otherwise. As used herein, the term "computer-implemented method" is synonymous with the term "software application" unless the context clearly dictates otherwise.

As used herein, the term "about" in conjunction with a numeral refers to a range of that numeral starting from 10% below the absolute of the numeral to 10% above the absolute of the numeral, inclusive.

Figure 1:
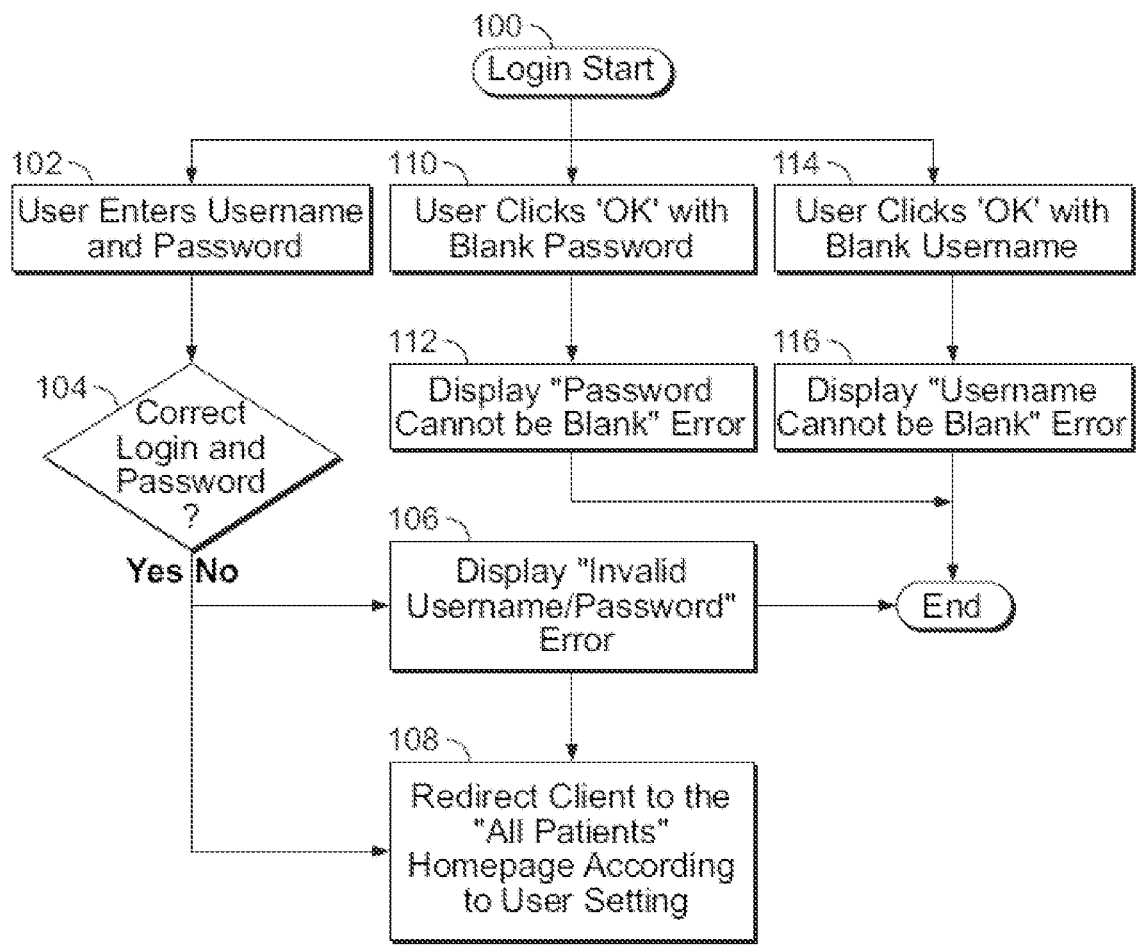
FIG. 1 is a flow diagram showing a method for logging into a computer-implemented method, in accordance with an embodiment of the present invention.
Figures 2A, 2B, 2C, 2D:
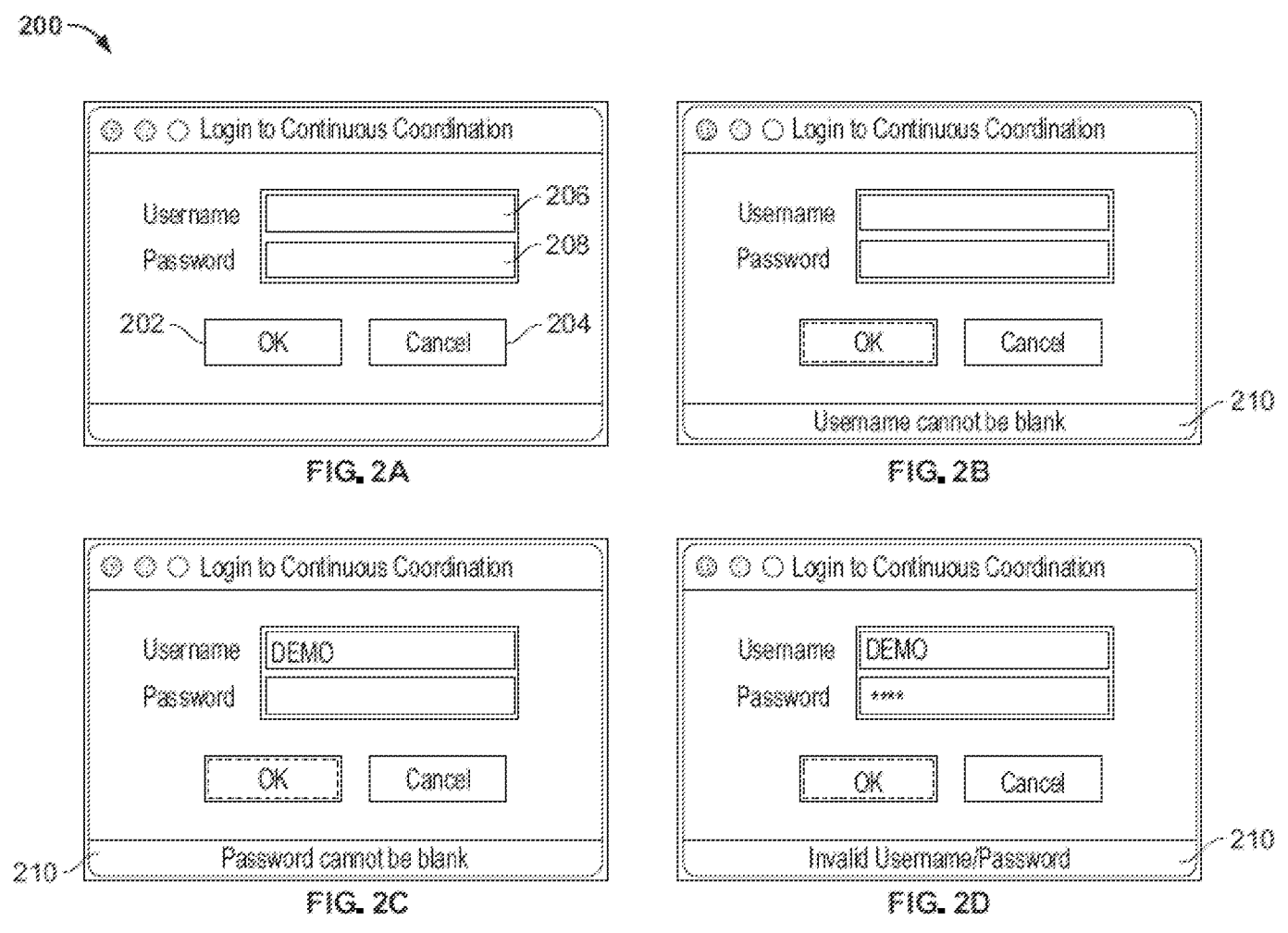

FIG. 1 shows a flowchart diagram of a user logging into a computer-implemented method. The user starts at a login screen 100, 200 when the computer-implemented method is opened on a computing device. In an embodiment, login screen 100 shows several areas for user input including, but not limited to, a username field 206, a password field 208, a confirmation button 202, a cancellation button 204, and a message box 210 (as shown in FIG. 2A). The computer-implemented method can receive user input from several peripherals including, but not limited to, a computer mouse, keyboard, or stylus. In the present embodiment, the computer-implemented method receives user input from a computer mouse and keyboard. Depending on the user input on login screen 100, a different result will occur. For example, step 102 occurs when the user inputs a username and a password. If the user selects confirmation button 202, then a verification step 104 will follow, that verifies the inputted username and password for accuracy based on a hospital's staff database. If the two user inputs do not match, then login screen 100 will display an error message in message box 210 depicting that the user input for the login is incorrect as shown in step 106. If the user inputs do match, then login screen 100 will redirect the user to a new screen showing a list of all patients in a hospital's patient database as shown in step 108.

In one embodiment, step 110 occurs when the user inputs a username and leaves password field 208 blank but selects confirmation button 202. Login screen 200 will display an error message in message box 210 depicting the user cannot leave password field 208 blank as shown in step 112. In an embodiment, step 114 occurs when the user selects confirmation button 202 without inputting information into username field 206 or password field 208. Also, step 114 can occur when the user selects confirmation button 202 after inputting information into password field 208, but not username field 206. After step 114 occurs, login screen 200 will display an error message in message box 210 illustrating username field 206 cannot be left blank as shown in step 116.

FIGS. 2A-D show exemplary configurations of login screen 100, 200 in FIG. 1. Upon opening the computer-implemented method, login screen 200 will appear as shown in FIG. 2A. Accordingly, username field 206, password field 208, and message box 210 will remain blank. FIG. 2B depicts the situation if step 114 and step 116 occur. In an embodiment, message box 210 in FIG. 2B shows an exemplary error message that would be displayed if the user selects confirmation button 202 without inputting information into username field 206. FIG. 2C shows login screen 200 if step 110 and step 112 occur. Message box 210 (see FIG. 2C) shows an exemplary error message that would be displayed if the user inputs information into the username field 206 but leaves password field 208 blank and selects confirmation button 202. FIG. 2D depicts the situation if steps 102, 104, and 106 occur. Message box 210 in FIG. 2D shows an exemplary error message that would be displayed if the user inputs an incorrect username and/or password into username field 206 or password field 208, respectively, and selects confirmation button 202.

FIG. 3 shows an exemplary configuration of main screen 300 comprising an active patient area 302, a patients list area 304, an all-patients button 306, a department list 308, an all-departments button 310, a procedure information area 312, a user information area 314, a date display 316, and an application logo 318.

In an exemplary embodiment, active patient area 302 displays the personal information for a selected patient from patients list area 304. If there is no active patient selected from patients list area 304, then active patient area 302 will display the format for the type of information that it displays as seen in FIG. 3. Active patient area 302 may include labels for, but is not limited to, the patient's name, date of birth, sex, height, weight, medical record number (MRN), admitted date, code status, class, allergies, financial encounter number (FIN), assigned room number, attending physician, bedside nurse, and current location. In the present embodiment, active patient area 302 includes labels for the patient's name, date of birth, sex, height, weight, MRN, admitted date, code status, class, allergies, FIN, assigned room number, attending physician, bedside nurse, and current location. If a user selects a label, main screen 300 will display information about the label. This information could be, but is not limited to, describing an acronym and/or uses for the label's information. For example, if a user selects MRN, main screen 300 will display information that MRN stands for medical record number.

All-patients button 306 will display all patients available in the hospital's patient database. If a user selects all-patients button 306, any filters for patients list area 304 would be removed. In an embodiment, department list 308 shows a list of departments that are available within the hospital's patient database. Each department has a separate button that will filter patients list area 304 when selected. Department list 308 includes, but is not limited to, surgery, radiology, laboratory, pharmacy, dialysis, telemetry, and therapy. In the present embodiment, the available departments are surgery, radiology, laboratory, pharmacy, dialysis, telemetry, and therapy. Procedure information area 312 displays the operation information for the patient(s) that are being filtered or selected. If there is no filter or active patient selected, then procedure information area 312 remains blank or displays a message indicating there is no information available. Accordingly, procedure information area 312 displays a message indicating there is no information available. Also, procedure information area 312 will display a message indicating there is no information available when an actively selected patient does not have an operation in the selected department. If a user selects all-departments button 310, the information in the procedure information area 312 will be removed. User information area 314 shows the username for the user that has logged in.

Figure 4:
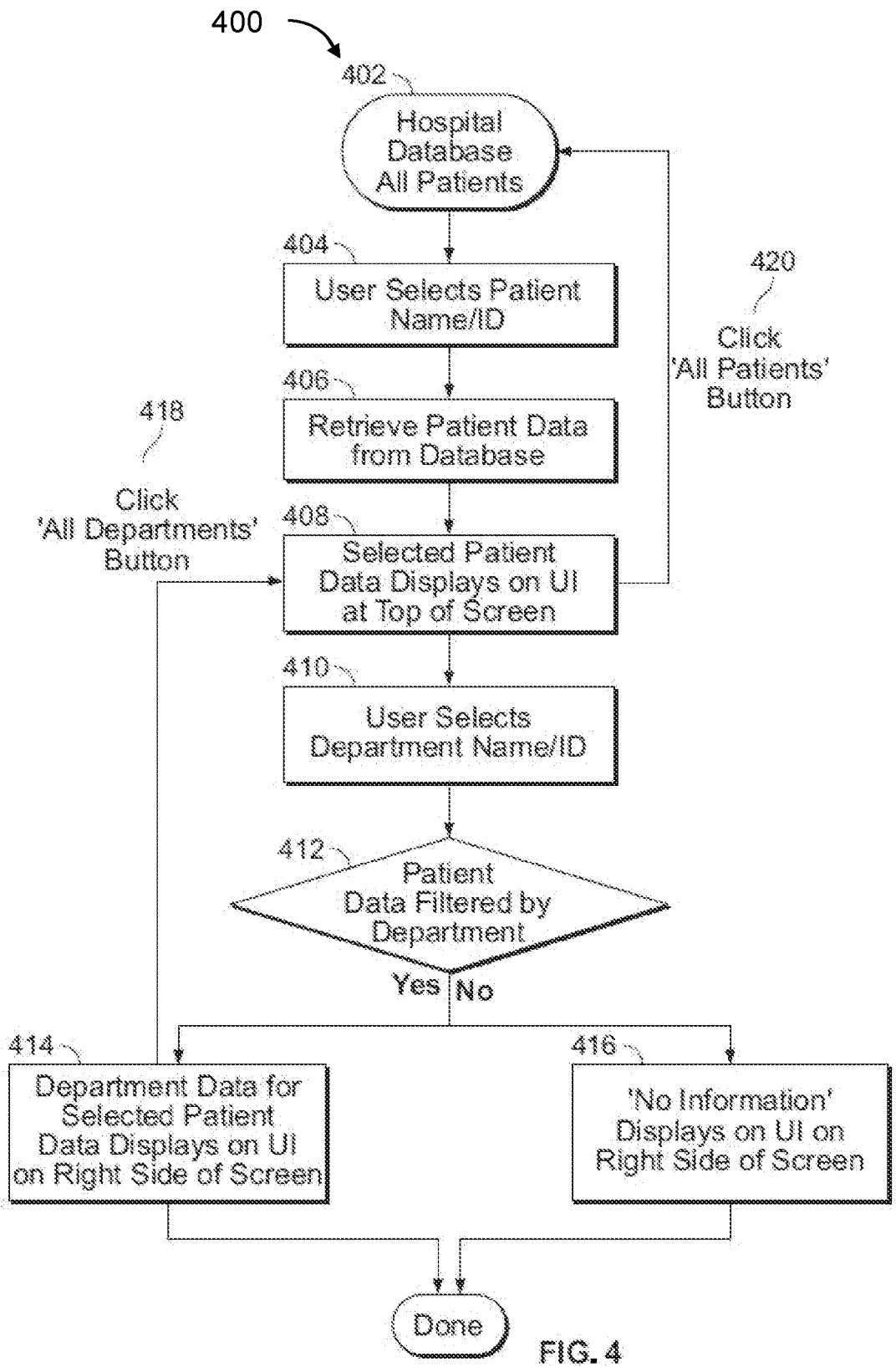
FIG. 4 is a flow diagram showing a method of obtaining information from the database based on a patient name/ID and filtering information for the patient based on a department.

FIG. 4 illustrates flowchart 400 for a user filtering information from the hospital's patient database based on the patient name/ID. As shown in step 402, the user begins with a list of all patients in patients list area 304 on main screen 300 (see FIG. 3). Step 404 occurs if a user selects a patient from patients list area 304. The computer-implemented method will take the patient name/ID selected and search the hospital's patient database to obtain the patient's information as shown by step 406. Once the computer-implemented method retrieves the patient's information inside of the hospital's patient database, the patient's information will be displayed in active patient area 302 as shown in step 408. If a user selects all-patients button 306 (FIG. 3), then main screen 300 will revert to step 402, displaying all available patients in the patients list area 304 as shown by step 420. Step 410 occurs if the user selects a department name/ID from department list 308 (FIG. 3). By selecting a department name/ID, the information for the selected patient is filtered to display the selected department's information in procedure information area 312 as shown in step 412. If there is a procedure scheduled for the selected patient in the selected department, then the procedure area 312 will display the patient's procedure information as shown by step 414. Step 416 occurs if there is no procedure information available for the selected patient in the selected department. Step 418 occurs if the user selects all-departments button 310, then the filter for department from step 412 will be removed and main screen 300 will return to displaying the patient's information as shown in step 408.

Figure 5:
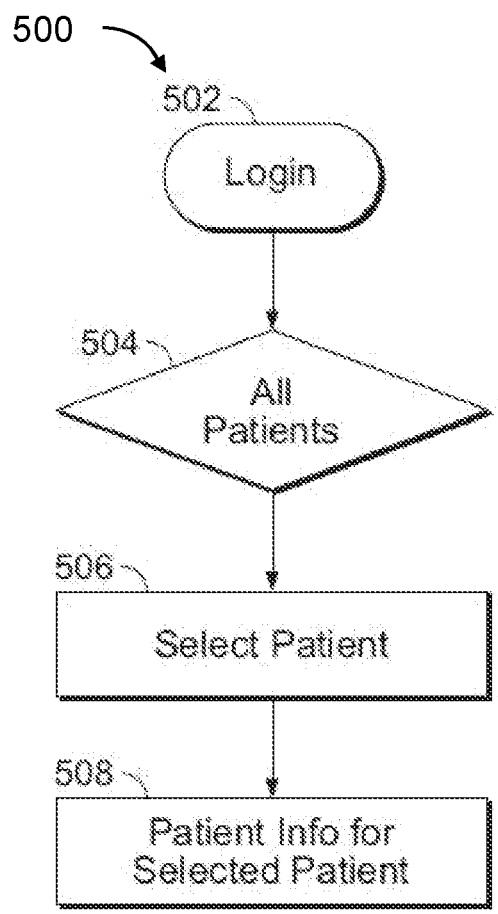
FIG. 5 is a flow diagram showing a method of filtering information for a patient's information.

Flowchart 500 illustrates the relevant selected steps to display a selected patient's information (see FIG. 5). After the user logs into the computer-implemented method through step 502, main screen 300 will display a list of all patients in patients list area 304 as shown in step 504. Step 506 will occur if the user selects a patient from patients list area 304 (FIG. 3). The application will display the information from the patient in active patient area 302 as shown in step 508.

FIG. 6 shows an exemplary configuration of main screen 300 with a selected patient 602. Since there is a selected patient, the patient information area 606 shows the selected patients' information instead of the format for the information as shown in FIG. 3. A selected patient will be highlighted as shown by selected patient 602. All-patients button 604 will display all patients available in the hospital's patient database. If a user selects all-patients button 604, the selected patient will be unselected. In an embodiment, department list 608 shows a list of departments that are available within the hospital's patient database. If a user selects an all-departments button 610, the operation information in the procedure information area 312 (see FIG. 3) will be removed.

Figure 7:
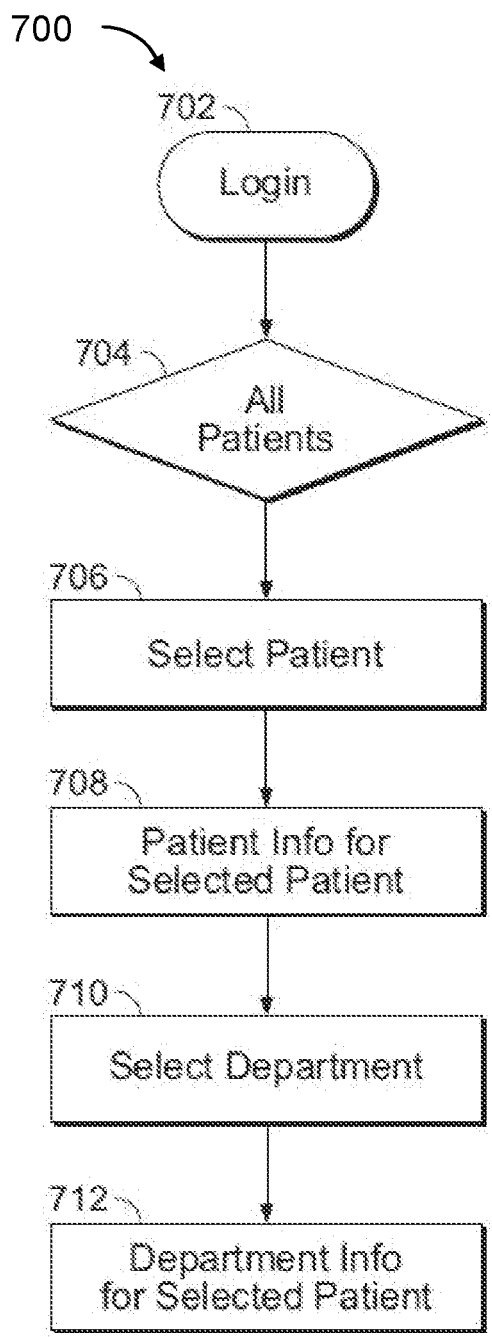
FIG. 7 is a flow diagram showing a method of filtering information from a database for a patient's procedure information.

Flowchart 700 shows the relevant selected steps to display a selected patient's operation information for a selected department by initially filtering by the patient's name/ID (FIG. 7). After the user logs into the computer-implemented method through step 702, main screen 300 will display all the available patients in patients list area 304 as shown in step 704. Step 706 will occur if the user selects a patient from the patients list area 304 (see FIG. 3). The computer-implemented method will display the information from the patient in the active patient 302 as shown in step 708. Step 710 occurs if the user selects a department from department list 308 (FIG. 3). After step 710 occurs, the computer-implemented method will display the department information of patient's procedure in the selected department as shown by step 712.

FIGS. 8A and 8B show exemplary configurations of the computer-implemented method where a patient's procedure information is displayed after selecting a department. FIG. 8A shows a patient 802 being selected from patients list area 304 (see FIG. 3) and a department 812 being selected from department list 808. After selecting patient 802 and department 812, procedure information area 814 will display patient's procedure information, if there is any. Procedure information 814 may include, but is not limited to, the patient's name, procedure, scheduled time, estimated wait time, room, and staff working on the procedure. In the present embodiment, procedure information area 814 displays the patient's name, procedure, scheduled time, estimated wait time, room, and staff working on the procedure. FIG. 8B shows what occurs when patient 802 does not have procedure information for the selected department. If there is no procedure information for patient 802 and department 812, then procedure information area 814 displays a message stating there is no available information. In the present embodiment, procedure information area 814 displays the message "No Information" when there is no available procedure information.

Figure 9:
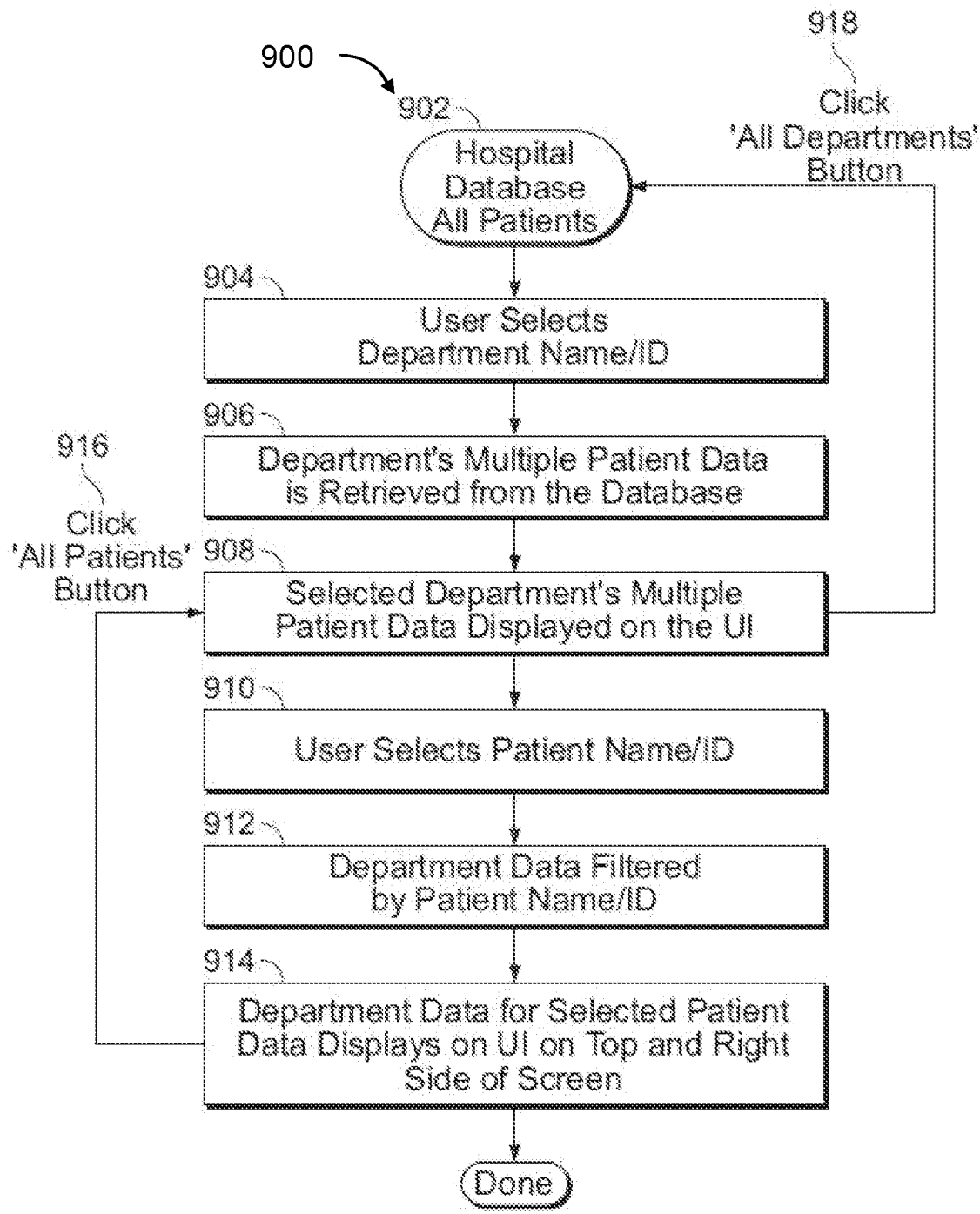
FIG. 9 is a flow diagram showing a method of obtaining information from the database based on a department name/ID and filtering information for the department based on a patient.

Flowchart 900 shows a user filtering information from the hospital's patient database based on the department name/ID (FIG. 9). As shown in step 902, the user begins with a list of all patients in patients list area 304 on main screen 300. Step 904 occurs if a user selects a department from department list 308 (see FIG. 3). The computer-implemented method will take the department name/ID selected and search the hospital's patient database to obtain the name of every patient that has a procedure scheduled for the selected department as shown by step 906. Once the computer-implemented method retrieves the list of patients inside of the hospital's patient database, every scheduled procedure will be displayed in procedure information area 312 as shown in step 908. If a user selects the all-departments button 310, then main screen 300 will revert to step 902, displaying all available patients in patients list area 304 as shown by step 918. Step 910 occurs if the user selects a patient name/ID from patients list area 304 (FIG. 3). By selecting a patient name/ID, the information for the selected department is filtered, as shown in step 912, to display only the selected patient's information in procedure information area 312 as shown in step 914. Step 916 occurs if a user selects all-patients button 306. The filter for the department from step 912 will be removed and main screen 300 will display all of the patients' procedures in procedure information area 312 as shown in step 908.

Figure 10:
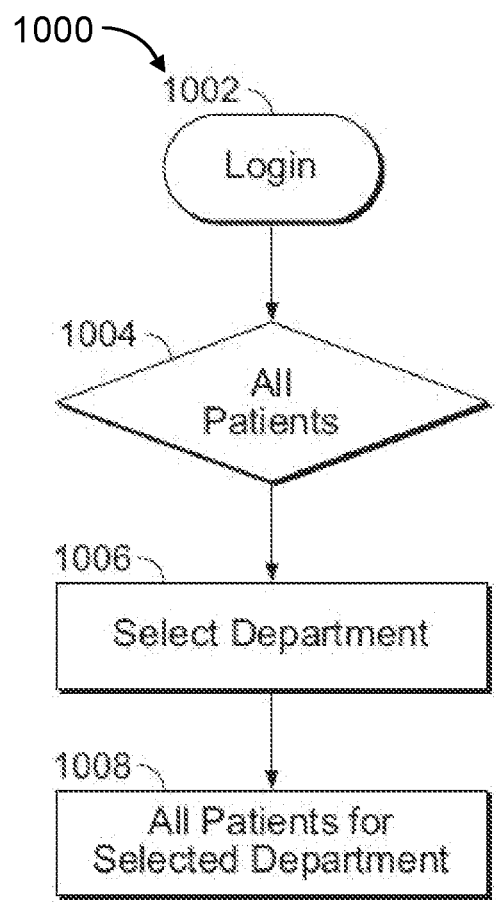
FIG. 10 is a flow diagram showing a method of filtering of information from the database for a selected department.

In one embodiment, flowchart 1000 shows the relevant selected steps to display all available patients for a selected department (see FIG. 10). After the user logs into the computer-implemented method through step 1002, main screen 300 will display a list of all patients in the patients list area 304 as shown in step 1004. Step 1006 will occur if the user selects a department from department list 308 (FIG. 3). The application will display the procedure information of all patients that have a scheduled procedure for the selected department in procedure information area 312 as shown in step 1008.

FIG. 11 shows an exemplary configuration of the computer-implemented method where the information from the hospital's patient database is filtered by department 1110 and all of the scheduled procedures are displayed in procedure information area 1112. The user can select department 1110 from department list 1106, which filters the information from the hospital's patient database and displays the procedure information of the filtered patients in procedure information area 1112. In this embodiment, active patient area 1104 continues to display the format for the type of information that it displays until a patient is selected. If a user selects all-patients button 1102, main screen 300 will display all patients with a procedure scheduled for department 1110. If a user selects an all-departments button 1108, the operation information in the procedure information area 1112 will be removed.

Figure 12:
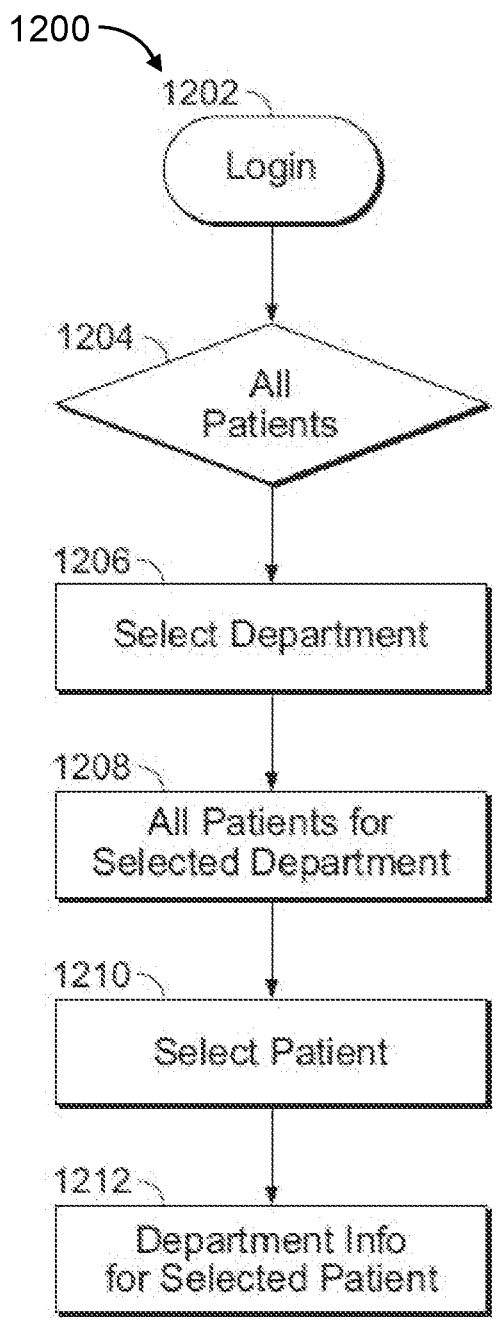
FIG. 12 is a flow diagram showing a method of filtering information from the database based on a selected department for a patient's procedure information.

In an embodiment, flowchart 1200 shows the relevant steps to display a selected patient's operation information for a selected department by initially filtering by the department name/ID (FIG. 12). After the user logs into the computer-implemented method through step 1202, main screen 300 will display a list of all patients in patients list area 304 as shown in step 1204. Step 1206 will occur if the user selects a department from department list 308 (see FIG. 3). The application will display a filtered list of patients in patients list area 304 that have an procedure scheduled for the selected department. Further, procedure information area 312 will display all scheduled procedures in the selected department as shown in step 1208. Step 1210 occurs if the user selects a patient from patients list area 304. After step 1210 occurs, the computer-implemented method will display only the patient's procedure information for the selected department as shown by step 1212.

FIGS. 13-19B show exemplary configurations of main screen 300 (see FIG. 3) being filtered by a department and selecting an available patient. The list of departments displayed on main screen 300 in department list 308 includes, but is not limited to, surgery, radiology, laboratory, pharmacy, dialysis, telemetry, therapy. In the present embodiment, main screen 300 displays the departments for surgery, radiology, laboratory, pharmacy, dialysis, telemetry, therapy. In an embodiment, FIG. 13 shows a selected patient 1302 being chosen from a filtered list of patients based on the selected department from the department list 1308. In the present embodiment, the selected department is surgery. Selected patient 1302 has their information displayed in patient information area 1306. Further, the selected patient 1302 has his/her/their information displayed in procedure information area 1312. Procedure information area 1312 may include, but is not limited to, the patient's name, procedure, scheduled time, estimated time of completion (ETC), estimated wait, room, surgeon, anesthesiologist, and pre-operation staff. In the present embodiment, procedure information area 1312 includes the patient's name, procedure, scheduled time, ETC, estimated wait, room, surgeon, anesthesiologist, and pre-operation staff. If a user selects all-patients button 1304, main screen 300 will display all patients with a procedure scheduled for the selected department. If a user selects an all-departments button 1310, the operation information in the procedure information area 1312 will be removed.

FIG. 14 shows a selected patient 1402 being chosen from a filtered list of patients based on the selected department. In the present embodiment, the selected department is radiology. Selected patient 1402 has his/her/their information displayed in procedure information area 1404. Procedure information area 1404 may include, but is not limited to, the patient's name, ordered imaging, scheduled time, estimated wait, queue, room, radiologist, transport technician, and whether someone will be at the patient's bedside. In the present embodiment, procedure information area 1404 includes the patient's name, ordered imaging, scheduled time, estimated wait, queue, room, radiologist, transport technician, and whether someone will be at the patient's bedside.

FIG. 15 shows a selected patient 1502 being chosen from a filtered list of patients based on the selected department. In the present embodiment, the selected department is laboratory. The selected patient 1502 has his/her/their information displayed in procedure information area 1504. Procedure information area 1504 may include, but is not limited to, the patient's name, lab order, scheduled time, estimated wait, queue, STAT order status, and phlebotomist. In the present embodiment, procedure information area 1504 includes the patient's name, lab order, scheduled time, estimated wait, queue, STAT order status, and phlebotomist.

FIG. 16 shows a selected patient 1602 being chosen from a filtered list of patients based on the selected department. In the present embodiment, the selected department is pharmacy. Selected patient 1602 has his/her/their information displayed in procedure information area 1604. Procedure information area 1604 may include, but is not limited to, the patient's name, medication details, scheduled time, estimated wait, queue, status, estimated time of arrival, and pharmacist. In the present embodiment, procedure information area 1604 includes the patient's name, medication details, scheduled time, estimated wait, queue, status, estimated time of arrival, and pharmacist.

FIG. 17 illustrates a selected patient 1702 being chosen from a filtered list of patients based on the selected department. In the present embodiment, the selected department is dialysis. Selected patient 1702 has his/her/their information displayed in procedure information area 1704. Procedure information area 1704 may include, but is not limited to, the patient's name, dialysis order, scheduled time, estimated wait, queue, nurse, and transport technician. In the present embodiment, procedure information area 1704 includes the patient's name, dialysis order, scheduled time, estimated wait, queue, nurse, and transport technician.

Figure 18:
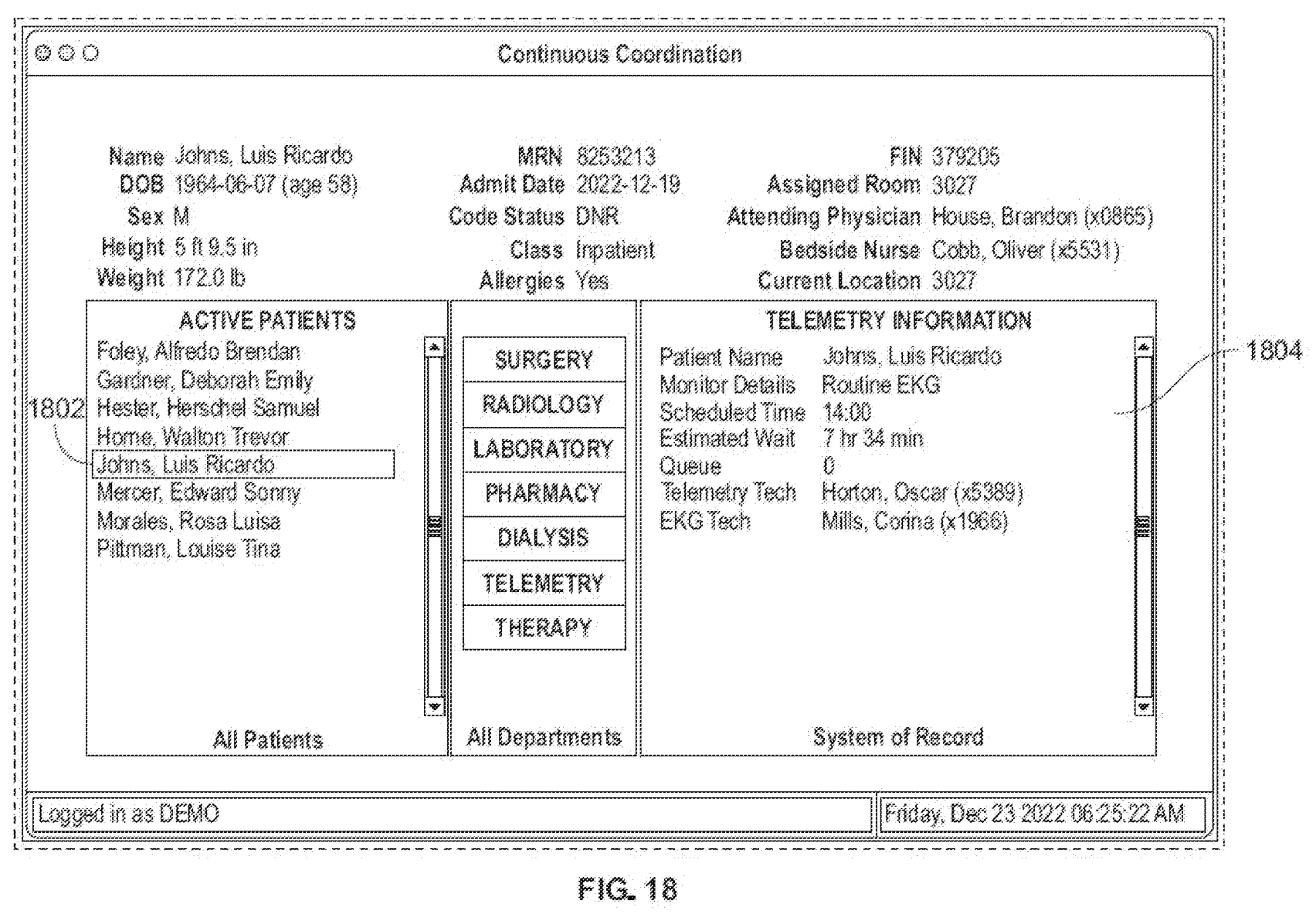

FIG. 18 depicts a selected patient 1802 being chosen from a filtered list of patients based on the selected department. In the present embodiment, the selected department is telemetry. Selected patient 1802 has his/her/their information displayed in procedure information area 1804. Procedure information area 1804 may include, but is not limited to, the patient's name, monitor details, scheduled time, estimated wait, queue, telemetry technician, and electrocardiogram (EKG) technician. In the present embodiment, procedure information area 1804 includes the patient's name, monitor details, scheduled time, estimated wait, queue, telemetry technician, and EKG technician.

Figure 19A:
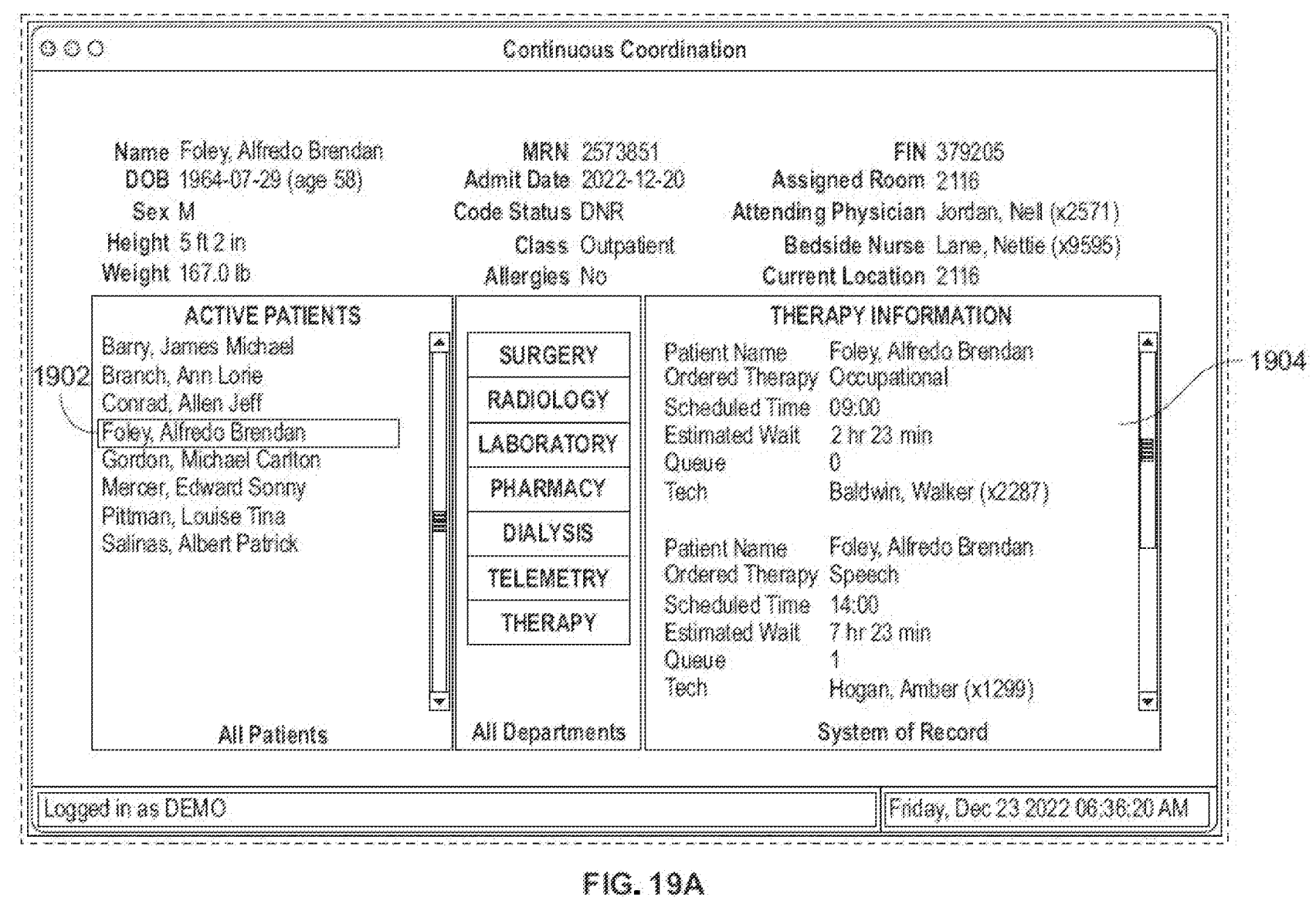

FIGS. 19A-B show a selected patient 1902 being chosen from a filtered list of patients based on the selected department. In the present embodiment, the selected department is therapy. Selected patient 1902 has his/her/their information displayed in procedure information area 1904. Procedure information area 1904 may include, but is not limited to, the patient's name, ordered therapy, scheduled time, estimated wait, queue, and technician. In the present embodiment, procedure information area 1904 includes the patient's name, ordered therapy, scheduled time, estimated wait, queue, and a technician. Further, procedure information area 1904 can display multiple procedures for the same patient. In the present embodiment, the procedure information area 1904 displays three therapy sessions for selected patient 1902. The user can scroll through the list of procedures in procedure information area 1904 using the scroll bar shown in FIGS. 19A-B.

Figure 20:
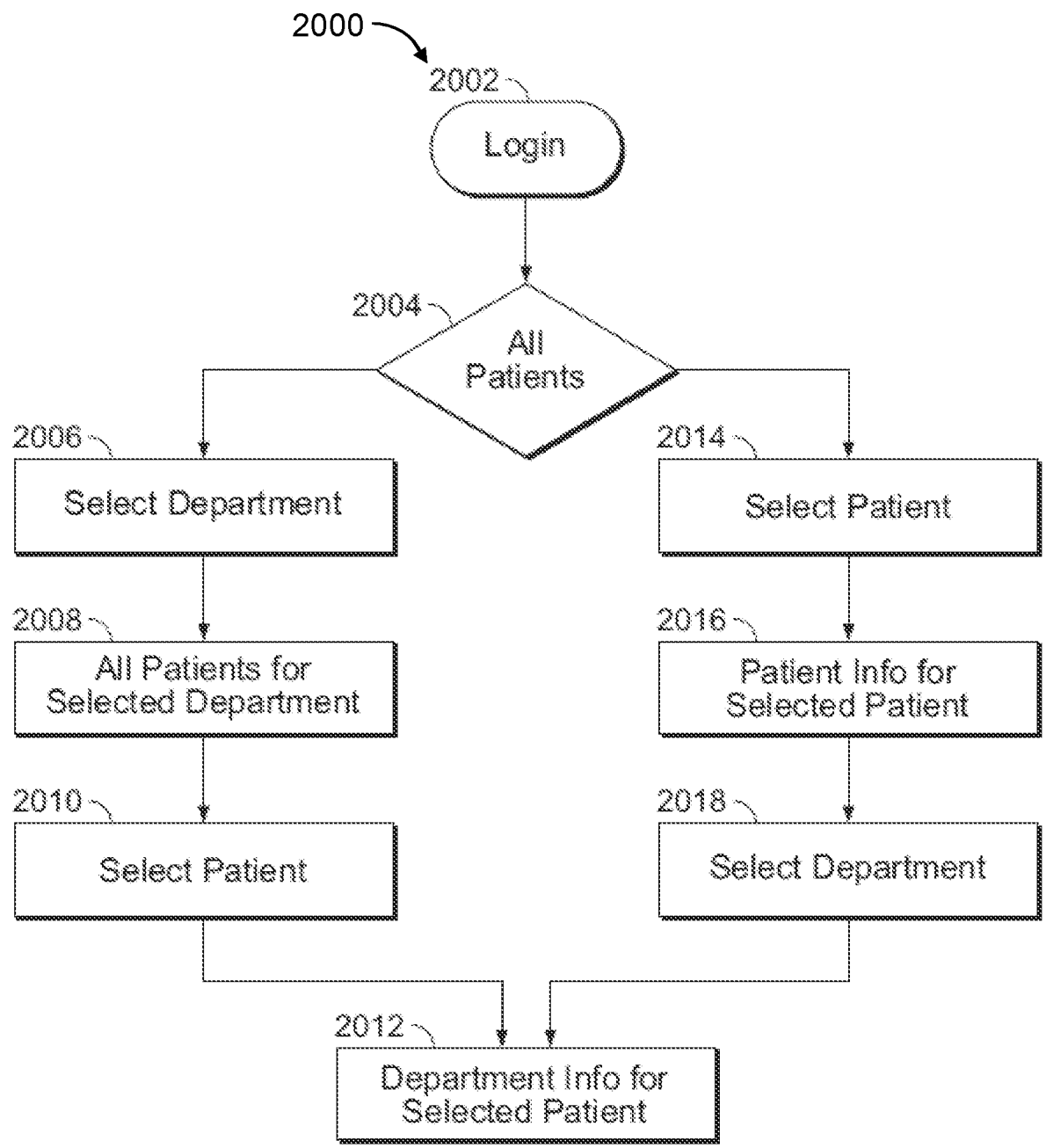
FIG. 20 is a flow diagram showing methods of filtering information from the database for a patient's procedure information.

In one exemplary embodiment, flowchart 2000 depicts a user's available filtering options upon logging into the computer-implemented method (FIG. 20). After the user logs into the computer-implemented method through step 2002, main screen 300 (see FIG. 3) will display all available patients in the hospital's patient database in the patients list area 304 as shown in step 2004. The user can choose to begin filtering the hospital's patient database information by department, as shown in step 2006, or by patient, as shown in step 2014. If the user filters by department, then the application will display a filtered list of patients in the patients list area 304 that have an procedure scheduled for the selected department. Further, procedure information area 312 will display all scheduled procedures in the selected department as shown in step 2008. Step 2010 occurs if the user selects a patient from patients list area 304. After step 2010 occurs, the computer-implemented method will display only the patient's procedure information in procedure area 312 for the selected department as shown by step 2012.

Alternatively, if the user initially filtered by a patient, as shown in step 2014, the application will display the information from the patient in active patient area 302 as shown in step 2016. Step 2018 occurs if the user selects a department from the department list 308. After step 2018 occurs, the computer-implemented method will display the patient's procedure information for the selected department in procedure information area 312 as shown by step 2012.

Figure 21:
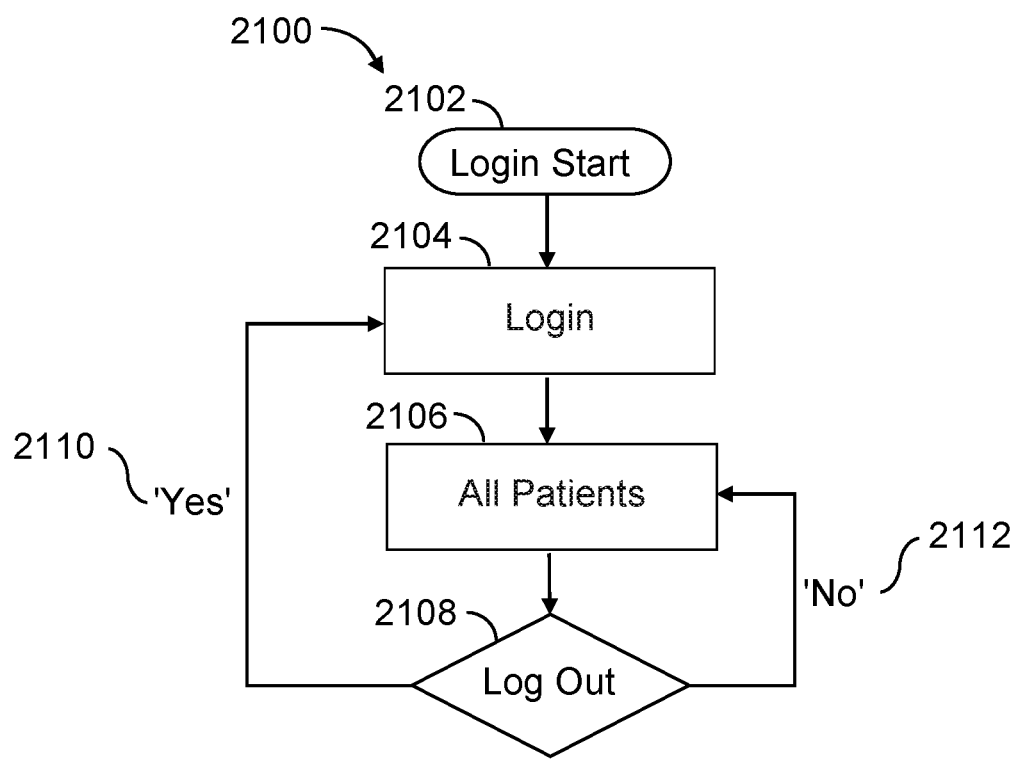
FIG. 21 is a flow diagram showing a method of logging out of a computer-implemented method, in accordance with an embodiment of the present invention.

Flowchart 2100 depicts a user logging into and logging out of the computer-implemented method (see FIG. 21). After the user starts the computer-implemented method, as shown in step 2102, the login screen 200 (FIG. 2) is displayed, as shown in step 2104. Once the user logs into the computer-implemented method, main screen 300 displays all available patients in the hospital's patient database in patients list area 304 as shown in step 2106. The user can logout of the computer-implemented method by selecting a logout option located in a file menu on the computing device. Upon selecting the logout option, the computer-implemented method displays two logout options, yes option 2110 or no option 2112. If the user selects yes option 2110, the user will be logged out of the computer-implemented method. Further, main screen 300 (see FIG. 3) will close and login screen 200 will be displayed. If the user selects no option 2112, the computer-implemented method will close the display for the two logout options and display main screen 300.

Thus, specific configurations of a computer-implemented method for organizing hospital staffing and medical information across multiple departments have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The invention claimed is:

1. A computer-implemented method for providing a user of a computing device access to patient information, scheduled procedures for the patient, and assigned staff for each procedure, the method comprising:
   (a) receiving, by one or more peripherals, a user input, said user input indicating a user command to affect a login screen and a main screen;

(b) displaying on said main screen information received from a connected patient database, said displayed information comprising an unfiltered list of patient names/IDs, a list of departments, and an active patient area, wherein
main screen is updated from said connected patient database that can be updated from several different computing devices;
(c) receiving, by one or more peripherals, a user selection of a patient's name from said unfiltered list of patient names;
(d) filtering information from said patient database displaying said selected patient's information in the active patient area; and
(e)
(i) receiving, by one or more peripherals, a user selection of an all- patients button, removing said filter for said previously selected patient from said data and returning the user to the main screen; or
(ii) receiving., by one or more peripherals, a user selection of a department from said list of departments, wherein information for the selected patient from said patient database is filtered to display the selected patient's procedures in said selected department in a procedure information area, and wherein upon further receiving, by one or more peripherals, a user selection of an all-departments button, the filter for said selected department is removed and the selected patient's procedures are removed from the procedure information area.

2. The method of claim 1, wherein the active patient area comprises at least the patient's name, attending physician, bedside nurse, and current location.

3. The method of claim 2, wherein the active patient area further comprises at least one of date of birth, sex, height, weight, medical record number (MRN), admitted date, code status, class, allergies, financial encounter number (FIN), and assigned room number.

4. The method of claim 1, further comprising a login screen, said login screen comprising a username field and a password field, wherein said username field and said password field are configured to receive said user input.

5. The method of claim 4, wherein said login screen comprises a confirmation button for checking said login information entered into said username field and said password field.

6. The method of claim 4, wherein said login screen is configured to display a message for issues with said user input in said username and/or password fields.

7. The method of claim 1, further comprising options for said user to logout out of said computer-implemented method, wherein a yes option logs user out and a no option keeps user logged in.

8. The method of claim 1, wherein said main screen is configured to display an updating date display.

9. The method of claim 1, wherein said main screen is configured to display an area showing a username for said user.

10. The method of claim 1, wherein said selected patient's procedure information displays a patient's number in a queue of other patients, wherein said queue can be updated from multiple computing devices.

11. The method of claim 1, wherein said main screen is configured to simultaneously display a procedure information area and an active patient area.

12. A computer-implemented method for providing a user of a computing device access to patient information, scheduled procedures for the patient, and assigned staff for each procedure, the method comprising:
(a) receiving, by one or more peripherals, user input, said user input indicating a user command to affect a login screen and a main screen;
(b) displaying on said main screen information received from a connected patient database, wherein said displayed information comprising an unfiltered list of patient names, a list of departments, and an active patient area, wherein said main screen is updated from said connected patient database that can be updated from several different computing devices;
(c) receiving, by one or more peripherals, a user selection of a department from said list of departments;
(d) filtering, based on the selected department, said information from said patient database displaying a filtered list of patients as well as displaying every scheduled procedure in a procedure information area; and
(e)
(i) receiving, by one or more peripherals, a user selection of an all-departments button, removing said filter for said selected department from said data and returning the user to the main screen; or
(ii) receiving, by one or more peripherals, a user selection of a patient name from said filtered list of patient names, wherein information for the selected patient from said patient database is filtered to display only the selected patient's procedures in said selected department in the procedure information area, and wherein upon further receiving, by one or more peripherals, a user selection of an all-patients button, the filter for said selected patient is removed and the user is returned to the screen comprising the filtered list of patient names as well as every scheduled procedure in the procedure information area.

13. The method of claim 12, further comprising a login screen, said login screen comprising a username field and a password field, wherein said username field and said password field are configured to receive said user input.

14. The method of claim 13, wherein:
i) said login screen comprises a confirmation button for checking said login information entered into said username field and said password field; and
ii) said login screen is configured to display a message for issues with said user input in said username and/or password fields.

15. The method of claim 12, further comprising options for said user to logout out of said computer-implemented method, wherein a yes option logs user out and a no option keeps user logged in.

16. The method of claim 12, wherein said main screen is configured to display an updating date display.

17. The method of claim 12, wherein said main screen is configured to display an area showing a username for said user.

18. The method of claim 12, wherein said selected patient's procedure information displays a patient's number in a queue of other patients, wherein said queue can be updated from multiple computing devices.

19. The method of claim 12, wherein said main screen is configured to simultaneously display a procedure information area and an active patient area.

20. The method of claim 12, wherein the active patient area comprises at least the patient's name, attending physician, bedside nurse, and current location.

21. The method of claim 20, wherein the active patient area further comprises at least one of date of birth, sex, height, weight, medical record number (MRN), admitted date, code status, class, allergies, financial encounter number (FIN), and assigned room number.

\* \* \* \* \*